(12) United States Patent
Kamerling et al.

(10) Patent No.: US 6,932,839 B1
(45) Date of Patent: Aug. 23, 2005

(54) INTRAOCULAR LENS ASSEMBLY AND METHOD

(76) Inventors: William Kamerling, 423 Clements Bridge Rd., Barrington, NJ (US) 08007; Joseph M. Kamerling, 423 Clements Bridge Rd., Barrington, NJ (US) 08007

(*) Notice: Subject to any disclaimer, the term of this patent is extended or adjusted under 35 U.S.C. 154(b) by 0 days.

(21) Appl. No.: 10/306,851

(22) Filed: Nov. 27, 2002

(51) Int. Cl.$^7$ ................................................ A61F 2/16
(52) U.S. Cl. .................... 623/6.24; 623/6.11; 623/6.37
(58) Field of Search ............................. 623/6.11, 6.38, 623/6.4, 6.43, 6.18, 6.19, 6.21, 6.37

(56) References Cited

U.S. PATENT DOCUMENTS

| | | | |
|---|---|---|---|
| 4,092,743 A | * | 6/1978 | Kelman ...................... 623/6.43 |
| 4,950,290 A | | 8/1990 | Kamerling |
| RE36,150 E | * | 3/1999 | Gupta ........................... 623/6 |
| 6,282,449 B1 | | 8/2001 | Kamerling |

FOREIGN PATENT DOCUMENTS

WO    WO 99/03427    *   1/1999    ............. A61F 2/16

OTHER PUBLICATIONS

S. O. Hansen, "Posterior Capsular Opacification and Intraocular Lens Decentration", Journal of Cataract and Refractive Surgery, vol. 14, No. 6, pp. 605-623 (Nov. 1988).*
Eye World, vol. 7, No. 8; Aug. 2002; pp. 30-34.
Eye World, vol. 7, No. 7; Jul. 2002; pp. 22-25.

* cited by examiner

Primary Examiner—Corrine McDermott
Assistant Examiner—Kamrin R. Landrem
(74) Attorney, Agent, or Firm—Stuart E. Beck

(57) ABSTRACT

An intraocular lens assembly and method. The assembly comprises an optic disc and an annulus surrounding the optic disc. Hinges connect the optic disc to the annulus to permit anterior and posterior movement of the optic disc relative to the annulus in response to contraction and relaxation of the ciliary muscle so that the eye accommodates to focus on a near object. The method comprises the steps of placing in the posterior chamber an optic disc and an annulus. The annulus surrounds the optic disc and is connected to it by hinges that permit anterior and posterior movement of the optic disc relative to annulus in response to contraction and relaxation of the ciliary muscle whereby said eye accommodates to focus on a near object.

12 Claims, 1 Drawing Sheet

INTRAOCULAR LENS ASSEMBLY AND METHOD

FIELD OF THE INVENTION

This invention relates to intraocular lenses, and more particularly, to an intraocular lens which can accommodate to permit near objects such as texts to be in focus.

BACKGROUND OF THE INVENTION

The subject matter of my earlier U.S. Pat. No. 4,950,290 granted on Aug. 21, 1990 and entitled POSTERIOR CHAMBER INTRAOCULAR LENS, and U.S. Pat. No. 6,282,449 granted on Aug. 28, 2001 and entitled IMPROVED METHOD AND DEVICE FOR CAUSING THE EYE TO FOCUS ON A NEAR OBJECT are incorporated in their entirety into this patent application.

Typically, the eye focuses on a near object by increasing the curvature of the lens. The change in curvature is called "accommodation." The objective of accommodation is to sharply focus an observed image on the retina.

The curvature of the lens is controlled by the circular fibers of the ciliary muscle. The ciliary muscle is an annulus that is connected to the lens by the zonules. When the ciliary muscle is relaxed the lens is flattened, i.e., it has less curvature. Thus distant objects are in focus.

Contraction of the ciliary muscle causes the zonules to relax and the lens to thicken, i.e., it has more curvature, thereby shortening its focal distance to accommodate the viewing of a near object.

Described in my earlier U.S. Pat. No. 6,282,449 is a method and device for dealing with the presbyopia of a natural lens. Thus, an aging natural lens becomes hardened and the ciliary muscle weakens thereby precluding or diminishing the ciliary muscle's ability to change the curvature of the lens so that the person will be able to focus on near objects.

However, the method and device described in U.S. Pat. No. 6,282,449 is not suitable when a non-accommodating intraocular lens replaces the natural lens such as after the removal of cataracts.

In my earlier U. S. Pat. No. 4,950,290 there is disclosed an intraocular lens and a method for implanting it in the posterior chamber. The lens described in that patent comprises an optic disc which is supported by a haptic which extends between the optic disc and the tissue supporting it to retain the optic disc in the desired location on the visual axis in the posterior chamber.

The use of a haptic to support an optic disc is well known. Haptics are discussed extensively in *Eye World*, Vol. 7, No. 8; August 2002; pgs. 30–34.

However, while haptic based intraocular lenses are well known, most have not been capable of accommodation. Further, because of the space required for the haptic in accommodating intraocular lenses, the optic discs of the prior art are no more than about 4.50 to 5.50 millimeters in diameter. With optic discs of such small diameter, several negative effects can occur. Thus, it is common for patient to see halos or to be annoyed by glare around the edge of the optic disc. Further, it is relatively easy for a small optic disc to become decenterd thereby diminishing its effectiveness or making it useless.

It is desirable to have an intraocular lens that can automatically accommodate to bring near objects into focus in response to contraction of the ciliary muscle as described in my earlier U.S. Pat. No. 6,282,449.

Further, it would be especially advantageous if such an intraocular lens were progressively multi-focal so as to avoid the need for wearing trifocal eyeglasses.

These objectives and advantages can be achieved by taking advantage of the fact the contraction of the ciliary muscle actually tends to reduce the volume of the posterior compartment slightly. Since the volume of the vitreous humor in the posterior compartment can not be reduced, it presses against the posterior capsule 16 and moves it slightly anteriorly.

It has been discovered that the vitreous humor can be used to cause relative movement between two parts of an intraocular lens assembly that is placed in the capsular bag so the eye focuses by moving the optic anteriorly (toward the near object) to focus instead of changing its curvature as disclosed in my U.S. Pat. No. 6,282,449. When focusing on a far object the ciliary muscle relaxes and the optic can move posteriorly to return to its previous position relative to the retina.

SUMMARY OF THE INVENTION

With the foregoing in mind, the invention relates to an intraocular lens assembly to be implanted in the posterior chamber and which moves anteriorly and returns posteriorly to return to its previous position to bring a near object or a far object into focus.

The assembly comprises an optic disc and an annulus. The annulus surrounds the optic disc and is connected to the optic disc by a plurality of hinges.

The hinges enable the optic disc to move anteriorly and posteriorly to return to its previous position relative to the retina and the annulus as the eye focuses on near or far objects.

In another aspect the invention relates to a method for enabling the eye to focus on a near object. The method comprises the steps of placing in the posterior chamber an assembly that includes an optic disc and an annulus. The annulus surrounds the optic disc and is connected to it by a plurality of hinges.

Contraction of the ciliary muscle causes the optic to move anteriorly relative to the annulus and the retina so that the eye can focus on a near object.

The lens assembly is implanted in the eye by making an incision in the wall of the eye. Then the lens assembly is folded or rolled so that its size is reduced and it is inserted through the incision into the posterior chamber. The lens assembly is then permitted to resume its shape.

BRIEF DESCRIPTION OF THE DRAWING

For the purpose of illustrating the invention there is shown in the drawings forms which are presently preferred, being understood, however, that the invention is not limited to the precise arrangements and instrumentality shown.

DETAILED DESCRIPTION OF PREFERRED EMBODIMENT

Figure 1:
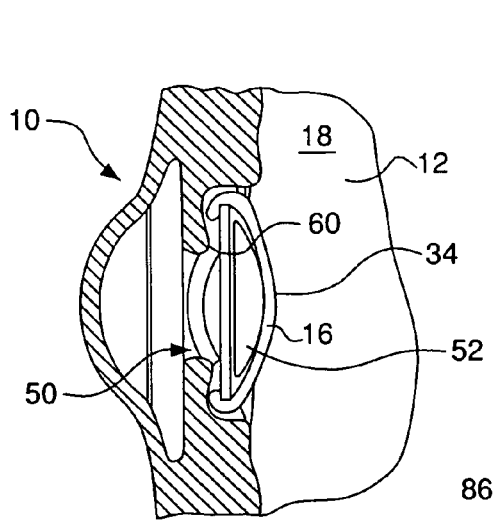
FIG. 1 is a sectional view through an eye showing an intraocular lens in accordance with the present invention implanted in the capsular bag.

Now referring to the drawing wherein like numerals indicate like elements FIG. 1 shows a partial cross section of an eye 10.

The eye 10 includes a posterior compartment partially shown at 12. The posterior compartment 12 supports the retina at its posterior (not shown) and the lens capsule 16 at its anterior. The posterior compartment 12 carries the vitreous humor 18.

Figure 2:
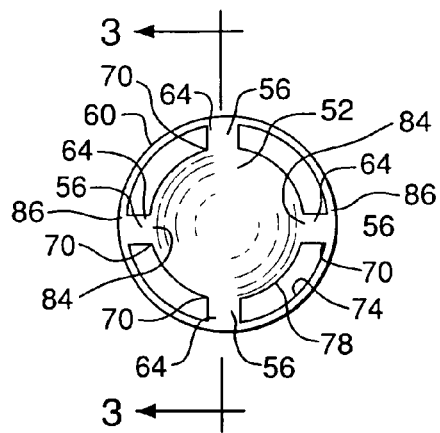
FIG. 2 is a front plan view of the intraocular lens constructed in accordance with the presently preferred form of the invention.

The intraocular lens assembly 50 of the invention is implanted in the posterior chamber 34 of the eye 10 after the nucleus (not shown) is removed. As best seen in FIG. 2, it includes an optic disc 52 which is connected by a plurality of hinges 56 to a haptic. The haptic is in the form of an annulus 60 which extends around the optic disc 52.

Advantageously, the optic disc 52 is about 7.00 millimeters in diameter. This has the effect of reducing the occurrence of the halos and glare that is common with optic discs of smaller diameter and assures better centration.

Further, the annulus 60 preferably has a diameter of about 12.00 millimeters. This permits the posterior capsule taut fit which helps to assure that the vitreous humor will push the optic to move anteriorly.

Preferably, the optic disc 52 is bi-convex as illustrated. However, for the purpose of the invention it need only be posterior convex.

Figure 3:
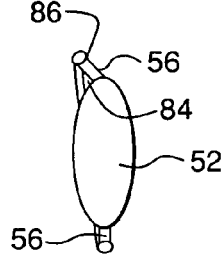
FIG. 3 is a sectional view taken along line 3—3 of FIG. 2.

As best seen in FIGS. 2 and 3, there may be provided four hinges 56 with each of the hinges 56 being relatively thin. At one end 64, the hinges 56 are connected to the interior periphery 74 of the annulus 60. At their other end 70, each of the hinges is connected to the exterior periphery 78 of the optic disc 52.

The juncture of ends 64 and 70, and interior periphery 74 and exterior periphery 78, define resilient flexible joints 84 and 86. The resilient flexible joints 84 and 86 are biased to retain the optic disc in the position it would occupy if the ciliary muscle were not contracted, i.e., its normal position, while enabling the optic disc 52 to move anteriorly when the ciliary muscle contracts and posteriorly to its normal position when the ciliary muscle relaxes.

Preferably, the annulus 60 is angled at about 10° anteriorly from the optic disc 52 as seen in FIG. 3. As explained in my earlier U.S. Pat. No. 4,950,290, the angular disposition of the annulus 60 relative to the optic disc 52 helps to reduce the likelihood of posterior capsular opacification.

The intraocular lens assembly 50 is implanted in the posterior chamber 34 by making a small incision. The lens assembly 50 is constructed from a transparent resilient material such as silicon or acrylic. Therefore, it can be folded or rolled so that it can fit through the incision and then after the annulus 60 is seated it returns to its original shape once it is placed in the eye.

The intraocular lens assembly 50 of the invention automatically accommodates when a patient reads. This is because the ciliary muscle contracts as if it were engaging a capsule 16 having a natural nucleus.

This contraction slightly reduces the volume of the posterior compartment 12. The vitreous humor 18 which is in the posterior compartment 12 is in engagement with the posterior wall of the posterior chamber 34. The reduction of the volume of the posterior compartment 12 causes the vitreous humor 18 to push the capsule 16 and the optic disc 52 anteriorly relative to the annulus 60 and the retina (not shown) causing accommodation. The movement of the optic disc 52 relative to the annulus 60 is enabled by the hinges 56.

The annulus 60 is stationary in the capsule 16 because it is fixed in the capsule 16 as described earlier.

The capsule 16 will not collapse under the pressure of the vitreous humor 18 because the wall of the posterior chamber is supported by the convex surface of the optic disc 52 and the annulus 60.

Figure 4:
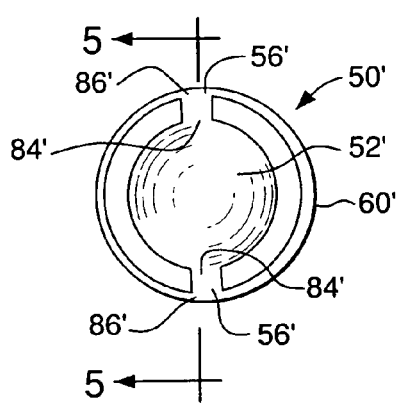
FIG. 4 is a front plan view of another form of the invention.
Figure 5:
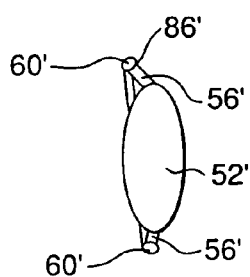
FIG. 5 is a sectional view taken along line 5—5 of FIG. 4.

Referring to FIGS. 4 and 5, another embodiment of the intraocular lens assembly 50' is shown.

The intraocular lens assembly 50' of this form of the invention is similar to that which has been described with respect to FIGS. 1–3. Therefore like parts are identified by the same reference numerals followed by a prime, i.e., '.

The form of the invention shown in FIGS. 4 and 5 has only two hinges 56' which are arranged vertically to provide upper and lower hinges.

In this form of the invention the flexibility of the joints 84' and 86' can be selected to achieve differing amounts of anterior movement with the same degree of ciliary muscle contraction. Thus, if joint 84' at the optic is flexible, there is less movement. However, if joint 86' at the annulus is flexible, then there is greater movement.

Still further, if joint 84' of the upper hinge is flexible and joint 86' of the lower hinge is flexible, the lower part of the optic will move more anteriorly than the upper part of the optic disc 52'. This will cause the optic disc 52' to rotate about a horizontal axis to tilt up to assist in looking at near and intermediate objects such that a progressive multi-focal lens is achieved.

Figure 6:
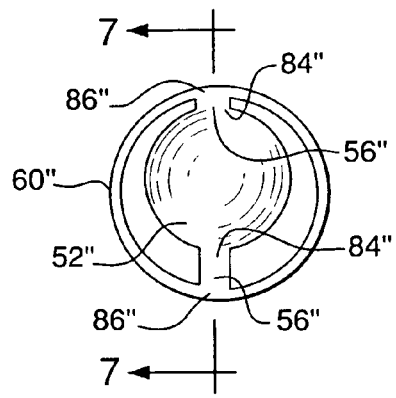
FIG. 6 is a front plan view of a further form of the invention.
Figure 7:
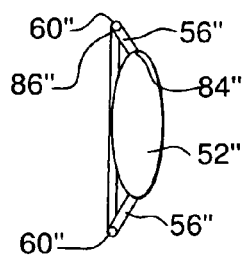
FIG. 7 is a sectional view taken along line 7—7 of FIG. 6.

A still further form of the invention is shown in FIGS. 6 and 7. In this form of the invention upper and lower hinges 56" are provided. However, the lower hinge 56" is longer than the upper hinge 56".

Therefore, when the intraocular lens moves anteriorly, the longer lower hinge 56" will permit the lower part of the optic disc 52" to move further anteriorly than the upper part of the optic disc 52" will move. In a manner similar to that just described the anterior movement of the intraocular lens will cause the optic disc 52" to rotate about a horizontal axis to tilt up to assist in looking at near and intermediate objects so that a progressive multi-focal lens is achieved.

Thus, a progressive multi-focal intraocular lens which is capable of being accommodated by using the ciliary muscle in a manner similar to a natural lens using two or more hinges and with various configurations of the flexibility of the joints between the annulus comprising the haptic and the optic disc has been provided.

Further, while the invention has been described with respect to a presently preferred form, it is apparent that other forms and embodiments will be obvious to those skilled in the art in view of the foregoing description. Thus, the invention should not be limited to foregoing description, but rather, only by the scope of the appended claims.

What is claimed is:

1. A progressively multi-focal intraocular lens assembly to be placed in the posterior chamber and that accommodates when the eye looks downward comprising
    an optic disc,
    an annulus, said annulus surrounding said optic disc,
    upper and lower hinges disposed, respectively, between the upper and lower portions of said annulus and the upper and lower portions of said optic disc, each of said hinges including two ends, one of said ends being connected to the interior periphery of said annulus to define a first joint and the other end being connected to exterior periphery of said optic disc to define a second joint, said hinges and said joints being operative to rotate said optic disc about a horizontal axis to tilt up to assist in looking at near and intermediate objects by permitting more anterior movement of the lower portion of said optic disc than the upper portion of said optic disc as it moves anteriorly and posteriorly relative to said annulus in response to contraction and relaxation of the ciliary muscle whereby said eye accommodates while progressively focusing on intermediate and near object.

2. An assembly as defined in claim 1 wherein
said lower hinge is longer than said upper hinge so that the lower portion of said optic disc moves further anteriorly than the upper portion of said optic disc when the ciliary muscle contracts so that the eye accommodates for viewing intermediate and near objects as the lens becomes progressively multi-focal.

3. An assembly as defined in claim 1 wherein
one of said first joints is flexible.

4. An assembly as defined in claim 1 wherein
one of said second joints is flexible.

5. An assembly as defined in claim 1 wherein
one of said first joints and one of said second joints are flexible so that the lower portion of said optic disc moves further anteriorly than the upper portion of said optic disc when the ciliary muscle contracts so that the eye accommodates for viewing intermediate and near objects as the lens becomes progressively multi-focal.

6. An assembly as defined in claim 1 wherein
said joint at the juncture of said optic disc and said upper hinge is flexible, and
said joint at juncture of said annulus and said lower hinge is flexible, so that the lower portion of said optic disc moves more anteriorly then the upper portion of said optic disk, thereby producing a progressive multi-focal accommodating intraocular lens.

7. A method for enabling the eye to progressively focus on intermediate and near objects comprising the steps of
placing in the posterior chamber an assembly including an optic disc and an annulus, said annulus surrounding said optic disc,
providing upper and lower hinges connecting, respectively, the upper and lower portions of the interior periphery of said annulus to the upper and lower portions of said optic disc,
providing each of said hinges with a joint at each end to connect said hinges to said annulus and to said optic disc, said hinges and said joints being operative to rotate said optic disc about a horizontal axis to tilt up to assist in looking at near and intermediate objects as it moves anteriorly and posteriorly relative to said annulus in response to contraction and relaxation of the ciliary muscle whereby said eye accommodates as it progressively focuses on intermediate and near objects.

8. A method as defined in claim 7 including
the step of providing that said lower hinge is longer than said upper hinge so that the lower portion of said optic disc moves further forward than the upper portion of said optic disc when the ciliary muscle contracts so that the eye accommodates for viewing as the lens becomes progressively multi-focal.

9. A method as defined in claim 7 including
the step of providing for one of said first joints to be flexible so that the lower portion of said optic disc moves further forward than the upper portion of said optic disc when the ciliary muscle contracts so that the eye accommodates for viewing as the lens becomes progressively multi-focal.

10. An assembly as defined in claim 7 wherein
one of said second joints is flexible so that the lower portion of said optic disc moves further forward than the upper portion of said optic disc when the ciliary muscle contracts so that the eye accommodates for viewing as the lens becomes progressively multi-focal.

11. A method as defined in claim 7 including
the step of providing for one of said first joints and one of said second joints to be flexible so that the lower portion of said optic disc moves further forward than the upper portion of said optic disc when the ciliary muscle contracts so that the eye accommodates for viewing as the lens becomes progressively multi-focal.

12. A method as defined in claim 7 including the steps of
providing that the joint at the juncture of said optic disc and said upper hinge is flexible,
providing that the joint at the juncture of said annulus and said lower hinge is flexible so that the lower portion of said optic disc moves more anteriorly then the upper portion of said the optic disk thereby producing a progressive multi-focal accommodating intraocular lens.

\* \* \* \* \*